(12) United States Patent
Belson et al.

(10) Patent No.: US 10,123,800 B2
(45) Date of Patent: *Nov. 13, 2018

(54) SURGICAL INCISION AND CLOSURE APPARATUS WITH INTEGRATED FORCE DISTRIBUTION

(71) Applicant: ZipLine Medical, Inc., Los Altos, CA (US)

(72) Inventors: Amir Belson, Los Altos, CA (US); Eric Storne, Menlo Park, CA (US); Eric T. Johnson, Temecula, CA (US); Robert R. Ragland, Temecula, CA (US); Phillip C. Burke, Pala, CA (US); Luke Clauson, Redwood City, CA (US)

(73) Assignee: ZipLine Medical, Inc., Campbell, CA (US)

( * ) Notice: Subject to any disclaimer, the term of this patent is extended or adjusted under 35 U.S.C. 154(b) by 598 days.

This patent is subject to a terminal disclaimer.

(21) Appl. No.: 13/665,160

(22) Filed: Oct. 31, 2012

(65) Prior Publication Data

US 2013/0296930 A1 Nov. 7, 2013

Related U.S. Application Data

(63) Continuation-in-part of application No. 13/286,757, filed on Nov. 1, 2011, now Pat. No. 8,323,313.

(51) Int. Cl.
*A61B 17/08* (2006.01)
*A61B 17/00* (2006.01)
(Continued)

(52) U.S. Cl.
CPC .......... *A61B 17/085* (2013.01); *A61B 17/08* (2013.01); *A61B 17/02* (2013.01); *A61B 17/0466* (2013.01);
(Continued)

(58) Field of Classification Search
CPC ....... A61B 17/08; A61B 17/085; A61B 17/02; A61B 2017/086; A61B 17/00884;
(Continued)

(56) References Cited

U.S. PATENT DOCUMENTS 2,012,755 A 8/1935 Muth
2,371,978 A 3/1945 Perham
(Continued)

FOREIGN PATENT DOCUMENTS

CN 1126430 A 7/1996
CN 1442119 A 9/2003
(Continued)

OTHER PUBLICATIONS dictionary.com definition of "fixed", accessed on Sep. 13, 2017, http://www.dictionary.com/browse/fixed.*
(Continued)

*Primary Examiner* — Christopher L Templeton
*Assistant Examiner* — Majid Jamialahmadi
(74) *Attorney, Agent, or Firm* — Wilson Sonsini Goodrich and Rosati, P.C.

(57) ABSTRACT

Apparatus for closing a surgical incision comprise a base having left and right panels, a force distribution structure coupled to each panel, and a closure component which releasably attaches to the force distribution structure to draw the inner edges of the panels together in order to close adhered tissue edges. The force distribution structures allow the inner edges of the panels to expand while restraining expansion of the outer edges of the panels and limiting elongation of the lateral dimension of the panels. The incision closure appliance may be placed on skin or other tissue prior to forming the incision to be available to close said incision at the end of the surgical procedure.

14 Claims, 10 Drawing Sheets

(51) Int. Cl.
*A61B 17/02* (2006.01)
*A61B 17/04* (2006.01)

(52) U.S. Cl.
CPC ... *A61B 17/083* (2013.01); *A61B 2017/00407* (2013.01); *A61B 2017/00884* (2013.01); *A61B 2017/081* (2013.01); *A61B 2017/086* (2013.01); *A61B 2017/088* (2013.01)

(58) Field of Classification Search
CPC .............. A61B 17/081; Y10T 24/44752; Y10T 24/45246; A61F 13/00038; A61F 13/0269; A61F 13/00; A61F 2013/00106; A61F 2013/00119; A61F 2013/00131; A61F 2013/00144; A61F 2013/00148
USPC ......... 606/213, 215–219; 602/41, 42, 53, 54
See application file for complete search history.

(56) References Cited

U.S. PATENT DOCUMENTS

| | | | |
|---|---|---|---|
| 2,747,248 A | 5/1956 | Mercer | |
| 3,118,201 A | 1/1964 | Beghetto, Jr. | |
| 3,487,836 A | 1/1970 | Niebel et al. | |
| 3,516,409 A | 6/1970 | Howell | |
| 3,698,395 A | 10/1972 | Hasson | |
| 3,863,640 A | 2/1975 | Haverstock | |
| 3,926,193 A * | 12/1975 | Hasson | A61B 17/085 606/218 |
| 3,933,158 A | 1/1976 | Haverstock | |
| 3,971,384 A * | 7/1976 | Hasson | A61B 17/085 606/218 |
| 3,972,328 A | 8/1976 | Chen | |
| 3,983,878 A | 10/1976 | Kawchitch | |
| 4,038,989 A | 8/1977 | Romero-Sierra et al. | |
| 4,114,624 A | 9/1978 | Haverstock | |
| 4,210,148 A | 7/1980 | Stivala | |
| 4,222,383 A | 9/1980 | Schossow | |
| 4,224,945 A | 9/1980 | Cohen | |
| 4,526,173 A | 7/1985 | Sheehan | |
| 4,531,521 A | 7/1985 | Haverstock | |
| 4,535,772 A | 8/1985 | Sheehan | |
| 4,539,990 A | 9/1985 | Stivala | |
| 4,576,163 A | 3/1986 | Bliss | |
| 4,605,005 A | 8/1986 | Sheehan | |
| 4,612,230 A | 9/1986 | Liland et al. | |
| 4,676,245 A | 6/1987 | Fukuda | |
| 4,702,251 A | 10/1987 | Sheehan | |
| 4,780,168 A | 10/1988 | Beisang et al. | |
| 4,871,367 A | 10/1989 | Christensen et al. | |
| 4,881,546 A | 11/1989 | Kaessmann | |
| 4,905,694 A | 3/1990 | Will | |
| 4,950,282 A | 8/1990 | Beisang et al. | |
| 4,966,605 A | 10/1990 | Thieler | |
| 4,976,726 A | 12/1990 | Haverstock | |
| 5,176,703 A | 1/1993 | Peterson | |
| 5,190,032 A | 3/1993 | Zacoi | |
| 5,259,835 A | 11/1993 | Clark et al. | |
| 5,306,236 A | 4/1994 | Blumenfeld et al. | |
| 5,336,219 A | 8/1994 | Krantz | |
| 5,377,695 A | 1/1995 | An Haack | |
| 5,514,155 A | 5/1996 | Daneshvar | |
| 5,533,519 A | 7/1996 | Radke et al. | |
| 5,562,705 A | 10/1996 | Whiteford | |
| 5,665,108 A | 9/1997 | Galindo | |
| 5,725,507 A | 3/1998 | Petrick | |
| 5,788,660 A | 8/1998 | Resnik | |
| 5,823,983 A | 10/1998 | Rosofsky et al. | |
| 5,843,123 A | 12/1998 | Brazeau | |
| 6,007,564 A | 12/1999 | Haverstock | |
| 6,033,654 A | 3/2000 | Stedronsky et al. | |
| 6,074,965 A * | 6/2000 | Bodenschatz | A61F 13/00038 428/295.4 |
| 6,126,615 A | 10/2000 | Allen et al. | |
| 6,176,868 B1 | 1/2001 | Detour | |
| 6,194,629 B1 * | 2/2001 | Bernhard | A61F 13/0273 128/882 |
| 6,689,100 B2 | 2/2004 | Connelly et al. | |
| 6,726,706 B2 | 4/2004 | Dominguez | |
| 7,066,182 B1 | 6/2006 | Dunshee | |
| 7,361,185 B2 | 4/2008 | O'Malley et al. | |
| 7,455,681 B2 * | 11/2008 | Wilke | A61B 17/0466 606/216 |
| 7,511,185 B2 | 3/2009 | Lebner | |
| 7,641,682 B2 | 1/2010 | Palmaz et al. | |
| 7,645,285 B2 | 1/2010 | Cosgrove et al. | |
| 7,799,042 B2 | 9/2010 | Williamson et al. | |
| 8,246,590 B2 | 8/2012 | Hu et al. | |
| 8,313,508 B2 | 11/2012 | Belson et al. | |
| 8,323,313 B1 * | 12/2012 | Belson | A61B 17/085 606/216 |
| 8,439,945 B2 | 5/2013 | Belson et al. | |
| 8,592,640 B2 | 11/2013 | Zepeda et al. | |
| 8,663,275 B2 | 3/2014 | O'Malley et al. | |
| 9,008,784 B2 | 4/2015 | Chan et al. | |
| 9,050,086 B2 | 6/2015 | Belson et al. | |
| 9,089,328 B2 * | 7/2015 | Belson | A61B 17/08 |
| 9,179,914 B2 | 11/2015 | Belson et al. | |
| 9,271,858 B2 | 3/2016 | Ben-Meir et al. | |
| 9,474,529 B2 | 10/2016 | Belson et al. | |
| 9,554,799 B2 | 1/2017 | Belson et al. | |
| 9,554,800 B2 | 1/2017 | Belson et al. | |
| 9,561,034 B2 | 2/2017 | Belson et al. | |
| 9,642,621 B2 | 5/2017 | Belson et al. | |
| 9,642,622 B2 * | 5/2017 | Belson | A61B 17/085 |
| 2002/0099315 A1 | 7/2002 | Lebner | |
| 2003/0065294 A1 | 4/2003 | Pickup et al. | |
| 2003/0108352 A1 | 6/2003 | Hellman | |
| 2003/0120198 A1 | 6/2003 | Barkell et al. | |
| 2003/0163160 A1 | 8/2003 | O'Malley et al. | |
| 2003/0220596 A1 | 11/2003 | Dunshee | |
| 2004/0072964 A1 | 4/2004 | Udding et al. | |
| 2004/0106904 A1 | 6/2004 | Gonnelli et al. | |
| 2004/0204740 A1 | 10/2004 | Weiser | |
| 2004/0210176 A1 | 10/2004 | Diana | |
| 2004/0260234 A1 | 12/2004 | Srinivasan et al. | |
| 2005/0020956 A1 * | 1/2005 | Lebner | A61B 17/085 602/42 |
| 2005/0020957 A1 | 1/2005 | Lebner | |
| 2005/0070956 A1 | 3/2005 | Rousseau | |
| 2005/0080453 A1 | 4/2005 | Lebner et al. | |
| 2005/0085757 A1 | 4/2005 | Santanello | |
| 2005/0153090 A1 | 7/2005 | Marchitto et al. | |
| 2005/0234485 A1 | 10/2005 | Seegert et al. | |
| 2005/0277959 A1 | 12/2005 | Cosgrove et al. | |
| 2005/0284801 A1 | 12/2005 | Tacklind | |
| 2006/0030886 A1 | 2/2006 | Clark | |
| 2006/0122522 A1 | 6/2006 | Chavan et al. | |
| 2006/0200198 A1 | 9/2006 | Riskin et al. | |
| 2006/0259033 A1 | 11/2006 | Nesbitt | |
| 2007/0026078 A1 | 2/2007 | Almarsson et al. | |
| 2007/0038247 A1 | 2/2007 | Lebner et al. | |
| 2007/0078366 A1 | 4/2007 | Haggstrom et al. | |
| 2007/0088339 A1 | 4/2007 | Luchetti | |
| 2007/0106277 A1 | 5/2007 | Hood et al. | |
| 2007/0141130 A1 | 6/2007 | Villaneuva et al. | |
| 2007/0179419 A1 | 8/2007 | Simpson | |
| 2007/0185432 A1 | 8/2007 | Etheredge | |
| 2007/0260278 A1 | 11/2007 | Wheeler et al. | |
| 2008/0033334 A1 | 2/2008 | Gurtner et al. | |
| 2008/0069855 A1 | 3/2008 | Bonutti | |
| 2008/0081951 A1 | 4/2008 | Frasier et al. | |
| 2008/0103550 A1 | 5/2008 | Wenzel et al. | |
| 2008/0114396 A1 * | 5/2008 | Cory | A61B 17/085 606/216 |
| 2008/0147115 A1 | 6/2008 | O'Malley et al. | |
| 2008/0161731 A1 | 7/2008 | Woods et al. | |
| 2008/0228219 A1 | 9/2008 | Weiser | |
| 2008/0287864 A1 | 11/2008 | Rosenberg | |
| 2009/0036922 A1 | 2/2009 | Riskin et al. | |
| 2009/0062531 A1 | 3/2009 | Kanda | |
| 2009/0099496 A1 | 4/2009 | Heegard et al. | |
| 2009/0149869 A1 | 6/2009 | Lhun | |
| 2009/0158131 A1 | 6/2009 | Choi et al. | |

(56) References Cited

U.S. PATENT DOCUMENTS

| | | | |
|---|---|---|---|
| 2009/0162531 A1 | 6/2009 | Nesbitt | |
| 2009/0177225 A1 | 7/2009 | Nunez et al. | |
| 2009/0264709 A1 | 10/2009 | Blurton et al. | |
| 2009/0299255 A1 | 12/2009 | Kazala et al. | |
| 2009/0299257 A1 | 12/2009 | Long et al. | |
| 2009/0299303 A1 | 12/2009 | Seegert | |
| 2010/0100022 A1* | 4/2010 | Greener | A61B 17/083 602/44 |
| 2010/0121286 A1 | 5/2010 | Locke et al. | |
| 2010/0228287 A1 | 9/2010 | Jeekel et al. | |
| 2010/0280545 A1 | 11/2010 | Fridman | |
| 2011/0077667 A1 | 3/2011 | Singhatat et al. | |
| 2011/0106026 A1 | 5/2011 | Wu et al. | |
| 2011/0144470 A1 | 6/2011 | Mazar et al. | |
| 2012/0016410 A1 | 1/2012 | Belson et al. | |
| 2012/0029266 A1 | 2/2012 | Holmes et al. | |
| 2012/0095502 A1 | 4/2012 | Bargon et al. | |
| 2012/0116279 A1 | 5/2012 | Munro et al. | |
| 2012/0116485 A1 | 5/2012 | Burgmann | |
| 2012/0203273 A1 | 8/2012 | Riskin et al. | |
| 2012/0221044 A1 | 8/2012 | Archibald et al. | |
| 2012/0226214 A1* | 9/2012 | Gurtner | A61F 13/00 602/53 |
| 2012/0232587 A1 | 9/2012 | Burke et al. | |
| 2013/0072969 A1 | 3/2013 | Zhang | |
| 2013/0108352 A1 | 5/2013 | Ruiz, Sr. et al. | |
| 2013/0178897 A1 | 7/2013 | Wu et al. | |
| 2013/0281885 A1 | 10/2013 | Rowbottom et al. | |
| 2013/0281981 A1 | 10/2013 | Shamir | |
| 2013/0282049 A1 | 10/2013 | Peterson et al. | |
| 2013/0331757 A1 | 12/2013 | Belson | |
| 2014/0074156 A1 | 3/2014 | Belson et al. | |
| 2014/0171849 A1 | 6/2014 | Fischell et al. | |
| 2014/0222070 A1 | 8/2014 | Belson et al. | |
| 2014/0228712 A1 | 8/2014 | Elliott et al. | |
| 2014/0278229 A1 | 9/2014 | Hong et al. | |
| 2014/0316323 A1 | 10/2014 | Kanevsky et al. | |
| 2015/0045700 A1 | 2/2015 | Cavanagh et al. | |
| 2015/0105423 A1 | 4/2015 | Haudenschild et al. | |
| 2015/0148653 A1 | 5/2015 | Fleig et al. | |
| 2015/0209563 A1 | 7/2015 | Amir | |
| 2015/0216527 A1 | 8/2015 | Belson et al. | |
| 2015/0309535 A1 | 10/2015 | Connor et al. | |
| 2015/0313593 A1 | 11/2015 | Patenaude et al. | |
| 2015/0351690 A1 | 12/2015 | Toth et al. | |
| 2016/0007909 A1 | 1/2016 | Singh et al. | |
| 2016/0095597 A1 | 4/2016 | Belson et al. | |
| 2016/0106931 A1 | 4/2016 | Belson et al. | |
| 2016/0114146 A1 | 4/2016 | Belson et al. | |
| 2016/0202755 A1 | 7/2016 | Connor | |
| 2016/0206311 A1 | 7/2016 | Belson et al. | |
| 2016/0206312 A1 | 7/2016 | Belson et al. | |
| 2016/0206313 A1 | 7/2016 | Belson et al. | |
| 2016/0213924 A1 | 7/2016 | Coleman et al. | |
| 2016/0220175 A1 | 8/2016 | Tam et al. | |
| 2016/0220252 A1 | 8/2016 | Belson et al. | |
| 2016/0242646 A1 | 8/2016 | Obma | |
| 2016/0249924 A1 | 9/2016 | Belson et al. | |
| 2016/0296149 A1 | 10/2016 | Polsky et al. | |
| 2016/0302721 A1 | 10/2016 | Wiedenhoefer et al. | |
| 2016/0310140 A1 | 10/2016 | Belson et al. | |
| 2017/0035422 A1 | 2/2017 | Belson et al. | |
| 2017/0042541 A1 | 2/2017 | Belson et al. | |
| 2017/0143341 A1 | 5/2017 | Belson et al. | |
| 2017/0156664 A1 | 6/2017 | Belson et al. | |

FOREIGN PATENT DOCUMENTS

| | | |
|---|---|---|
| CN | 1524507 A | 9/2004 |
| CN | 1234327 C | 1/2006 |
| CN | 1234327 C | 1/2006 |
| CN | 101938944 A | 1/2011 |
| CN | 202537562 U | 11/2012 |
| CN | 202537562 U | 11/2012 |
| CN | 102946812 A | 2/2013 |
| CN | 104755033 A | 7/2015 |
| CN | 104825200 A | 8/2015 |
| EP | 1600108 A2 | 11/2005 |
| GB | 1401877 A | 8/1975 |
| JP | S5094788 | 7/1975 |
| JP | S62243557 A | 10/1987 |
| JP | H07502913 A | 3/1995 |
| JP | 2001-149485 A | 6/2001 |
| JP | 2005512678 A | 5/2005 |
| JP | 2005532134 A | 10/2005 |
| JP | 2010504835 A | 2/2010 |
| JP | 2013515417 A | 5/2013 |
| JP | 2013538603 A | 10/2013 |
| WO | WO-8401805 A1 | 5/1984 |
| WO | WO 96/29013 A1 | 9/1996 |
| WO | WO-03053296 A1 | 7/2003 |
| WO | WO 2006/124671 A2 | 11/2006 |
| WO | WO-2007004603 A1 | 1/2007 |
| WO | WO 2007/044647 A2 | 4/2007 |
| WO | WO 2008/019051 A2 | 2/2008 |
| WO | WO 2008/060532 A2 | 5/2008 |
| WO | WO-2009066116 A1 | 5/2009 |
| WO | WO 2011/019859 A2 | 2/2011 |
| WO | WO 2011/019859 A3 | 4/2011 |
| WO | WO 2011/043786 A1 | 4/2011 |
| WO | WO 2011/139912 A1 | 11/2011 |
| WO | WO 2011/159623 A1 | 12/2011 |
| WO | WO 2013/067024 A1 | 5/2013 |
| WO | WO-2014066879 A2 | 5/2014 |
| WO | WO-2014070922 A1 | 5/2014 |
| WO | WO-2015012887 A1 | 1/2015 |
| WO | WO-2015103556 A1 | 7/2015 |
| WO | WO-2015168165 A1 | 11/2015 |
| WO | WO-2017027075 A1 | 2/2017 |
| WO | WO-2017044120 A1 | 3/2017 |
| WO | WO-2017181059 A1 | 10/2017 |
| WO | WO-2017184825 A1 | 10/2017 |

OTHER PUBLICATIONS

Merriam-webster definition of "integral", accessed on Sep. 13, 2017, https://www.merriam-webster.com/dictionary/integral.*
U.S. Appl. No. 13/874,046, filed Apr. 30, 2013, Belson et al.
International search report and written opinion dated Mar. 19, 2013 for PCT/US2012/062820.
European search report and opinion dated Apr. 29, 2015 for EP Application No. 10822334.8.
International search report and written opinion dated Apr. 29, 2015 for PCT/US2015/010188.
Office action dated Apr. 7, 2015 for U.S. Appl. No. 13/685,909.
Office action dated Jun. 5, 2015 for U.S. Appl. No. 13/874,046.
Office action dated Jun. 17, 2014 for U.S. Appl. No. 13/414,176.
Office action dated Aug. 18, 2014 for U.S. Appl. No. 14/180,564.
European search report and written opinion dated Aug. 12, 2015 for EP Application No. 12844746.3.
Notice of allowance dated Sep. 22, 2015 for U.S. Appl. No. 13/414,176.
Hasson, et al. A new sutureless technique for skin closure. Arch Surg. Jan. 1976;111(1):83-4.
International search report and written opinion dated Sep. 10, 2014 for PCT/US2014/016587.
Office action dated Aug. 28, 2014 for U.S. Appl. No. 14/180,524.
Office action dated Sep. 19, 2014 for U.S. Appl. No. 13/685,909.
Co-pending U.S. Appl. No. 14/851,059, filed Sep. 11, 2015.
International search report and written opinion dated Sep. 30, 2015 for PCT Application No. US2015/28066.
Notice of allowance dated Dec. 19, 2014 for U.S. Appl. No. 14/180,564.
Office action dated Dec. 19, 2014 for U.S. Appl. No. 13/685,909.
U.S. Appl. No. 13/414,176, filed Mar. 7, 2012, Belson et al.
U.S. Appl. No. 13/685,909, filed Nov. 27, 2012, Belson.
International search report dated Jul. 30, 2010 for PCT/US2010/000430.

(56) References Cited

OTHER PUBLICATIONS

International search report and written opinion dated Jul. 29, 2011 for PCT/US2011/034649.
International search report and written opinion dated Oct. 21, 2011 for PCT Application No. US11/40213.
Office action dated Mar. 21, 2012 for U.S. Appl. No. 13/286,378.
Office action dated Mar. 23, 2012 for U.S. Appl. No. 13/286,757.
Office action dated May 2, 2012 for U.S. Appl. No. 13/096,602.
Office action dated Jul. 23, 2012 for U.S. Appl. No. 13/286,378.
Office action dated Jul. 23, 2012 for U.S. Appl. No. 13/286,757.
Office action dated Nov. 19, 2012 for U.S. Appl. No. 13/096,602.
Notice of allowance dated Jan. 17, 2013 for U.S. Appl. No. 13/096,602.
Notice of allowance dated Sep. 17, 2012 for U.S. Appl. No. 13/286,378.
Notice of allowance dated Sep. 20, 2012 for U.S. Appl. No. 13/286,757.
Office action dated Mar. 21, 2014 for U.S. Appl. No. 13/414,176.
U.S. Appl. No. 14/625,366, filed Feb. 18, 2015, Belson et al.
Office action dated Feb. 26, 2015 for U.S. Appl. No. 13/414,176.
U.S. Appl. No. 14/180,524, filed Feb. 14, 2014, Belson et al.
U.S. Appl. No. 14/180,564, filed Feb. 14, 2014, Belson et al.
European search report and opinion dated Jan. 7, 2014 for EP Application No. 11796253.0.
European search report and opinion dated Jan. 7, 2014 for EP Application No. 11778067.6.
International search report and written opinion dated Feb. 6, 2014 for PCT/US2013/067563.
Notice of allowance dated Feb. 10, 2015 for U.S. Appl. No. 14/180,524.
Office action dated Oct. 14, 2015 for U.S. Appl. No. 13/685,909.
Co-pending U.S. Appl. No. 14/958,803, filed Dec. 3, 2015.
Co-pending U.S. Appl. No. 14/958,818, filed Dec. 3, 2015.
International search report and written opinion dated Jan. 12, 2016 for PCT Application No. US2015/049671.
K984204, 510(k) Premarket Notification Summary, Silverlon™ Direct Pressure Wound Closure Strip, May 19, 2007.
Office action dated Mar. 4, 2016 for U.S. Appl. No. 13/874,046.
Co-pending U.S. Appl. No. 15/081,526, filed Mar. 25, 2016.
Co-pending U.S. Appl. No. 15/081,550, filed Mar. 25, 2016.
Co-pending U.S. Appl. No. 15/081,595, filed Mar. 25, 2016.
Co-pending U.S. Appl. No. 15/130,149, filed Apr. 15, 2016.
Co-pending U.S. Appl. No. 15/096,083, filed Apr. 11, 2016.
Co-pending U.S. Appl. No. 15/130,764, filed Apr. 15, 2016.
Merriam-Webster Dictionary. Definition of "lateral". Http://www.merriam-webster.com/dictionary/lateral. Accessed on May 5, 2016.
Notice of allowance dated Jun. 21, 2016 for U.S. Appl. No. 15/081,526.
Office action dated May 11, 2016 for U.S. Appl. No. 15/081,595.
Office action dated May 12, 2016 for U.S. Appl. No. 15/081,550.
Office action dated May 26, 2016 for U.S. Appl. No. 15/081,526.
Office action dated May 31, 2016 for U.S. Appl. No. 15/096,083.
Office action dated Jun. 17, 2016 for U.S. Appl. No. 15/130,149.
Co-pending U.S. Appl. No. 15/337,768, filed Oct. 28, 2016.
Co-pending U.S. Appl. No. 15/369,293, filed Dec. 5, 2016.
European search report and opinion dated Jul. 12, 2016 for EP Application No. 13851258.
International search report and written opinion dated Aug. 30, 2016 for PCT/US2016/028297.
Notice of allowance dated Feb. 23, 2016 for U.S. Appl. No. 15/081,595.
Notice of allowance dated Sep. 30, 2016 for U.S. Appl. No. 15/130,149.
Notice of allowance dated Oct. 5, 2016 for U.S. Appl. No. 15/096,083.
Notice of allowance dated Oct. 14, 2016 for U.S. Appl. No. 15/081,550.
Notice of allowance dated Dec. 19, 2016 for U.S. Appl. No. 15/130,149.
Office action dated Jul. 20, 2016 for U.S. Appl. No. 15/130,764.
Office action dated Nov. 17, 2016 for U.S. Appl. No. 15/081,595.
Zip® Surgical Skin Closure. Fast, non-invasive alternative to staples, sutures and glue. Accessed Aug. 17, 2016. http://www.ziplinemedical.com/products/zip-surgical-skin-closure/.
European search report and opinion dated Feb. 17, 2017 for EP Application No. 140829202.
European search report with written opinion dated Jul. 12, 2016 for EP13851258.
International search report with written opinion dated Jul. 14, 2017 for PCT/US2017/027695.
International search report with written opinion dated Jul. 18, 2017 for PCT/US2017/028537.
International search report with written opinion dated Aug. 30, 2016 for PCT/US2016/028297.
Notice of allowance dated Feb. 21, 2017 for U.S. Appl. No. 14/625,366.
Office action dated Feb. 1, 2017 for U.S. Appl. No. 15/130,764.
Office action dated Jun. 1, 2017 for U.S. Appl. No. 15/442,382.
Office action dated Jul. 27, 2017 for U.S. Appl. No. 14/851,059.
PCT/US2017/059286 International Search Report and Written Opinion dated Mar. 6, 2018.
U.S. Appl. No. 14/851,059 Notice of Allowance dated Mar. 14, 2018.
Extended European search report and opinion dated Jul. 27, 2017 for EP Application No. 15733186.
Office action dated Aug. 24, 2017 for U.S. Appl. No. 14/958,803.
Office Action dated Sep. 26, 2017 for U.S. Appl. No. 13/685,909.
Office Action dated Oct. 5, 2017 for U.S. Appl. No. 14/958,818.
Office Action dated Nov. 22, 2017 for U.S. Appl. No. 15/130,764.
Office Action dated Nov. 28, 2017 for U.S. Appl. No. 15/442,382.
"Notice of Allowance dated Jun. 20, 2018 for U.S. Appl. No. 15/130,764.".
"Office action dated Jun. 6, 2018 for U.S. Appl. No. 15/201,088.".
"U.S. Appl. No. 14/958,803 Notice of Allowance dated Apr. 4, 2018".
U.S. Appl. No. 14/958,803 Notice of Allowance dated May 11, 2018.

* cited by examiner

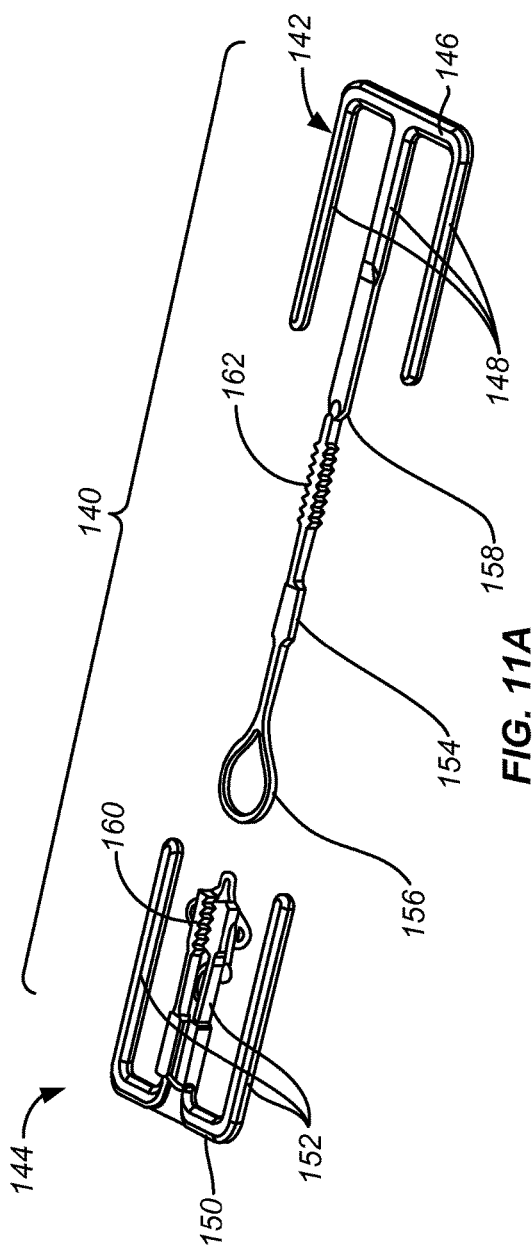
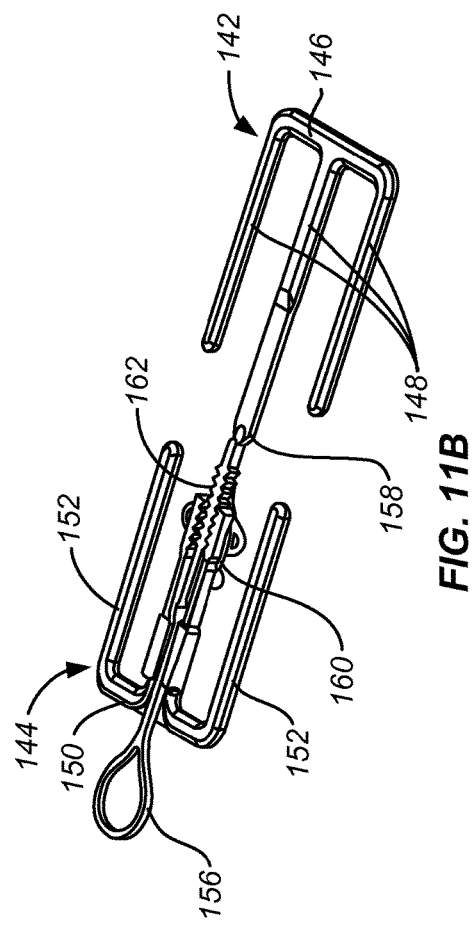
FIG. 11A
FIG. 11B

SURGICAL INCISION AND CLOSURE APPARATUS WITH INTEGRATED FORCE DISTRIBUTION

CROSS-REFERENCE TO RELATED APPLICATIONS

This application is a continuation-in-part of U.S. patent application Ser. No. 13/286,757, filed Nov. 1, 2011, the full disclosure of which is incorporated herein by reference.

BACKGROUND OF THE INVENTION

1. Field of the Invention

The present invention relates generally to medical apparatus and methods. More particularly, present invention relates to apparatus and methods for forming and closing surgical incisions.

Surgical closure devices including an adhesive based patch with right and left panels are known. Of particular interest of the present invention, such devices are described in co-pending, commonly owned PCT application US 2010/000430, full disclosure which is incorporated herein by reference. As described in the PCT application, an adhesive patch is placed over a patient's skin at a site where it is desired to form a surgical incision. After the patch is placed, an incision is formed along an axial line extending through the middle of the patch. After it is formed, the incision can be opened to perform a desired procedure, and after the procedure is completed the incision may be closed by drawing the inner edges of the panels together with a clip, zipper, or other closure member.

The principal objective of such surgical closure devices is to improved healing and reduce scaring from the incision. This objective, however, has been inhibited by certain characteristics of the presently available devices. For example, the tissue edges are not always brought together along an even line, which can increase the eventual scaring. Many such closure devices do not have the ability to adjust the closure force or distance on the tissue edges, limiting the ability to slightly "pucker" tissue which has been found to reduce scaring. Other shortcomings of the available incision and wound closure devices include difficulty of use and inability to conform to tissue manipulation during subsequent surgical protocols, i.e. those devices which are sufficiently rigid to securely close the tissue are often unable to conform to the tissue movement during the surgical procedure.

A particular problem arises with self-adhesive wound closure patches when they're used beneath an adherent surgical incision drape. Such drapes are used to help maintain the sterility of a tissue surface during a surgical procedure, and the drapes may be placed over a previously positioned tissue closure patch. As the surgical incision drape has an adhesive lower surface which adheres to the tissue, the drape will adhere to an upper surface of an underlying tissue closure patch. Removal of the surgical incision drape will thus often remove or at least displace a previously placed tissue closure patch. If any significant portion of the tissue closure patch is removed or displaced, the patch will no longer be useful for closing a surgical wound.

For these reasons, it would be desirable to provide improved surgical incision closure devices and methods for their use. It would be particularly desirable to provide incision closure devices which are able to adhere to the tissue, allow formation of the incision, conform to the deformation of the tissue during a subsequent surgical procedure, and provide controlled closure of the adjacent tissue edges subsequent to the procedure. In particular, it would be desirable if the incision closure devices were able to provide for the control and the uniform distribution of closure forces on the tissue edges while causing minimum restraint or stretching of the tissue during the surgical procedure. It would be still further desirable to provide improved surgical incision closure devices and methods for their use where the devices will resist removal and dislocation when used beneath a surgical incision drape. At least some of these objectives will be met by the inventions described below.

2. Description of the Background Art

Co-pending, commonly owned PCT application US 2010/000430 as been described above. Other surgical closure devices are described in the following U.S. Pat. Nos. 2,012,755; 3,516,409; 3,863,640; 3,933,158; 4,114,624; 3,926,193; 4,535,772; 4,676,245; 4,881,546; 4,905,694; 5,377,695; and 7,455,681; and U.S. Patent Publication Nos. 2005/0020956 and 2008/0114396. Commercial incision closure devices available from Ethicon, a division of Johnson & Johnson, under the trade name Ethizip™ temporary abdominal wound closure device.

SUMMARY OF THE INVENTION

The present invention provides improved apparatus and methods for closing wounds, particularly wounds resulting from incisions performed during surgical procedures. The incisions would usually be formed in a patient's skin, such as through the abdomen, but in some cases could also be on internal organs, within the oral cavity, within body cavities, or alike.

The devices and methods of the present invention will present minimum disruption of or interference with the surgical procedure which is performed after the incision is made. In particular, the devices and methods will permit the opposed edges of the incised tissue to be opened, stretched, and freely deformed with minimal restraint resulting from the presence of the closure device. Once the procedure has been completed, however, the devices and methods of the present invention will provide for a uniform distribution of closure forces to draw the tissue edges together in a manner which and minimize scaring. In particular, the closure devices can draw the tissue edges together at a slightly closer spacing than initially present at the forming of the incision in order to upwardly evert the tissue edges cause a "pucker" which can reduce scaring.

The devices and methods of the present invention will also be able to avoid or reduce disruption when a incision closure appliance is used beneath surgical incision drape which must be removed from over the closure appliance. A sacrificial layer is provided over at least part of the upper surface of the closure appliance, where the sacrificial cover is held in place while the surgical incision drape is placed over the incision closure appliance. After the incision and surgical procedure have been completed, the surgical incision drape will be pulled from the patient's skin. Instead of adhering to and dislodging the tissue closure appliance, the surgical drape adheres to the sacrificial cover, and only the sacrificial cover is pulled from the patient with the drape, leaving the remainder of the incision closure appliance in place.

In a first aspect of the present invention, an incision closure appliance comprises a base including a left panel and a right panel. Each panel has a tissue adherent lower surface, an upper surface, an inner edge, and an outer edge. The lower tissue adherent surface will typically be coated at least partially with a common tissue-adherent adhesive such as those used in surgical bandages and patches.

The incision closure appliance further includes a force distribution structure coupled to each panel (i.e. each panel will have at least one force distribution structure coupled thereto), where each force distribution structure is adapted to allow axial expansion of the panel along the inner edge while limiting lateral expansion over the entire length and axial expansion along the outer edge. By permitting axial expansion of the panel along the inner edge, the tissue edges are minimally constrained to allow the tissue to deform when stretched during the surgical procedure. Conversely, by limiting both lateral expansion and axial expansion along the outer edge, the panel will be able to apply a controlled and distributed closure force when the panels are drawn together after the surgical procedure is complete, as described in more detail below.

The incision closure appliance still further includes a closure component or assembly which attaches to the force distribution structure to draw the inner edges of the panels together after they had been adhered to the tissue on opposite sides of an incision site and the surgical procedure completed. Each panel of the base will typically comprise an at least partially elastic matrix, typically having an isotropic elasticity (i.e. the panel stretches evenly in all directions) but optionally having an anisotropic elasticity (where the matrix stretches preferentially in one direction or over a portion thereof). The elastic matrix may comprise an elastomeric membrane or sheet (for example Polyurethane sheet or Thermo Plastic Elastomers (TPE)), a woven fabric (typically woven at least partially from elastomeric filaments, threads, or fibers), a spun fabric, or the like. In certain embodiments, the elastomeric matrix may comprise a fabric woven from both elastic elements (typically threads, filaments, fibers, or the like) and having inelastic elements disposed along the outer edge and extending laterally there across in order to provide the expansion characteristics described above with respect to the force distribution structure. That is, in some cases, the force distribution structure may include or consist of inelastic elements woven or otherwise incorporated within a fabric membrane.

Typically, the force distribution structure will comprise a separate component of the incision closure appliance, for example including a spine disposed axially adjacent to the outer edge of the panel and a plurality of axially spaced-apart lateral supports disposed laterally and extending from the spine toward the inner edge of the panel. Such a "comb-like" structure will typically be formed from flexible but non-distensible materials so that the elements can flex together with the tissue deformation but will not stretch along their lengths so that they may provide dimensional stability in the lateral direction as well as along the outer edge of the panel. Examples of such materials include Nylon, Polypropylene, Polyethylene and Polycarbonate or other thermo polymers. Notably, the force distribution structure will not limit the axial stretching of the inner edge of the panel in order to provide the desired expansibility and conforms to the tissue during the surgical procedure. Such separate force distribution structures may be attached to the upper surface of the panel, or alternatively may be embedded in or laminated within the panel. Typically, the force distribution structure will not extend into or past the lower surface of the panel so that it will not interfere with adherence of the panel to the skin or other tissue.

The assembly of the base panels and the force distribution structures will typically be carried on a removable backing which covers and protects the adherent surface of the panels prior to use. The adherent backing may be removed in order to apply the base to the skin or other tissue at the site of the surgical intervention. Additionally, the right and left panels will typically be held together by removable tabs, an axial strip, or other removable covers or structures in order to hold the inner edges of the panel at a pre-determined distance or spacing as they are being adhered to the tissue. For example, removable tabs may be placed at each axial end of the base to temporarily secure the two base panels together. Alternatively, a removable strip or tape may be placed over an axial gap between the right and left panels to hold the panels in place relative to each other as the base is being adhered to the tissue surface. Such tabs or strips will typically be self-adhesive so that they may be secured to the panels and then removed by simply pulling off after the panels are properly placed. The cover, tabs, or strip may then be removed to leave the panels in place but unconnected prior to forming the surgical incision therebetween.

A first exemplary construction of the closure component or assembly comprises a right engagement member, a left engagement member, and a plurality of lateral struts holding the engagement members laterally apart by a pre-determined distance. The right engagement member is adapted to releasably engage the supports of the right panel along an inner edge thereof, and the left engagement member is adapted to releasably engage the supports of the left panel along an inner edge thereof. In the specific embodiments, at least some of the supports of the force distribution component will have cleats near their inner edges, and the engagement members will have slots which receive the cleats. After the surgical intervention is complete, the closure component may then be placed over the force distribution structure with the cleats on one side first being engaged by an engagement member and then the opposite engagement member being pulled over the cleats on the opposite side.

Alternatively, the closure component or assembly may comprise a plurality of independent lateral ties attached to at least some of the lateral supports. Such lateral ties are configured to be secured between the lateral supports, typically being fixed to one panel and being adjustably attachable to the other panel. For the exemplary embodiments, the adjustably attachable end may comprise a ratchet tightening mechanism or similar structure which allows each lateral tie to be independently adjusted at a different spacing between the right and left panels. In this way, the right and left panels may be differentially tensioned along their inner edges in order to control and optimize the forces applied to the adjacent tissue edges which are being drawn together.

Optionally, the closure appliance of the present invention may further comprise a securing layer which is adapted to be placed over the assembly of the base and the closure component after the assembly has been secured over an incision on a patient's skin and the surgical procedure has been completed. A securing layer will typically have a self-adhesive lower surface which can be placed over the assembly of the base and closure component to help secure it in place and to maintain cleanliness. The securing layer may optionally have openings to permit access to the wound for observation, delivery of antiseptics, and the like.

In a further aspect of the present invention, methods for forming an incision in tissue comprise providing an incision closure appliance as described above. The right and left panels of the appliance are adhered to the patient's skin, where the inner edges of the panels are spaced-apart by a pre-selected distance typically from 0.5 mm to 15 mm. An incision (typically linear) is formed in the tissue or skin surface between the inner edges of the panels, and the edges of the incised tissue are then separated to perform a desired surgical procedure. The inner edges of the panels can stretch and conform along with movement and deformation of the tissue edges while the outer edge and lateral extent of each panel remain dimensionally stable. After the procedure is complete, the closure component is secured to the force distribution structure to draw the inner edges of the panels back together. Optionally, the closure component has dimensions (or an adjustable inter-panel spacing) which draw the tissue edges closer together than they were immediately after the incision was formed. Such drawing together of the tissue causes the edges to evert and the tissue to "pucker" which can reduce scarring.

BRIEF DESCRIPTION OF THE DRAWINGS

FIGS. 11A and 11B illustrate an alternative lateral tie construction which can be used in the appliances of either FIG. 1 or FIG. 9.

DETAILED DESCRIPTION OF THE INVENTION

The apparatus and methods of the present invention will be used during both the formation and the closure of surgical incisions made to a patient's skin or other tissue during surgical procedures. As described hereinafter, the direction of the incision will define both "axial" and "lateral" directions as those terms are used herein. Most incisions will be made along a generally straight line which will define the axial direction. The lateral direction will generally be across the axial direction, typically but not necessarily being perpendicular or normal to the axial direction. Most incisions will be generally linear but in some cases the incisions could be curved or have other geometries. The term "axial" will then apply to the direction of the incision at any particular location, resulting in lateral directions which could also vary.

Figure 1:
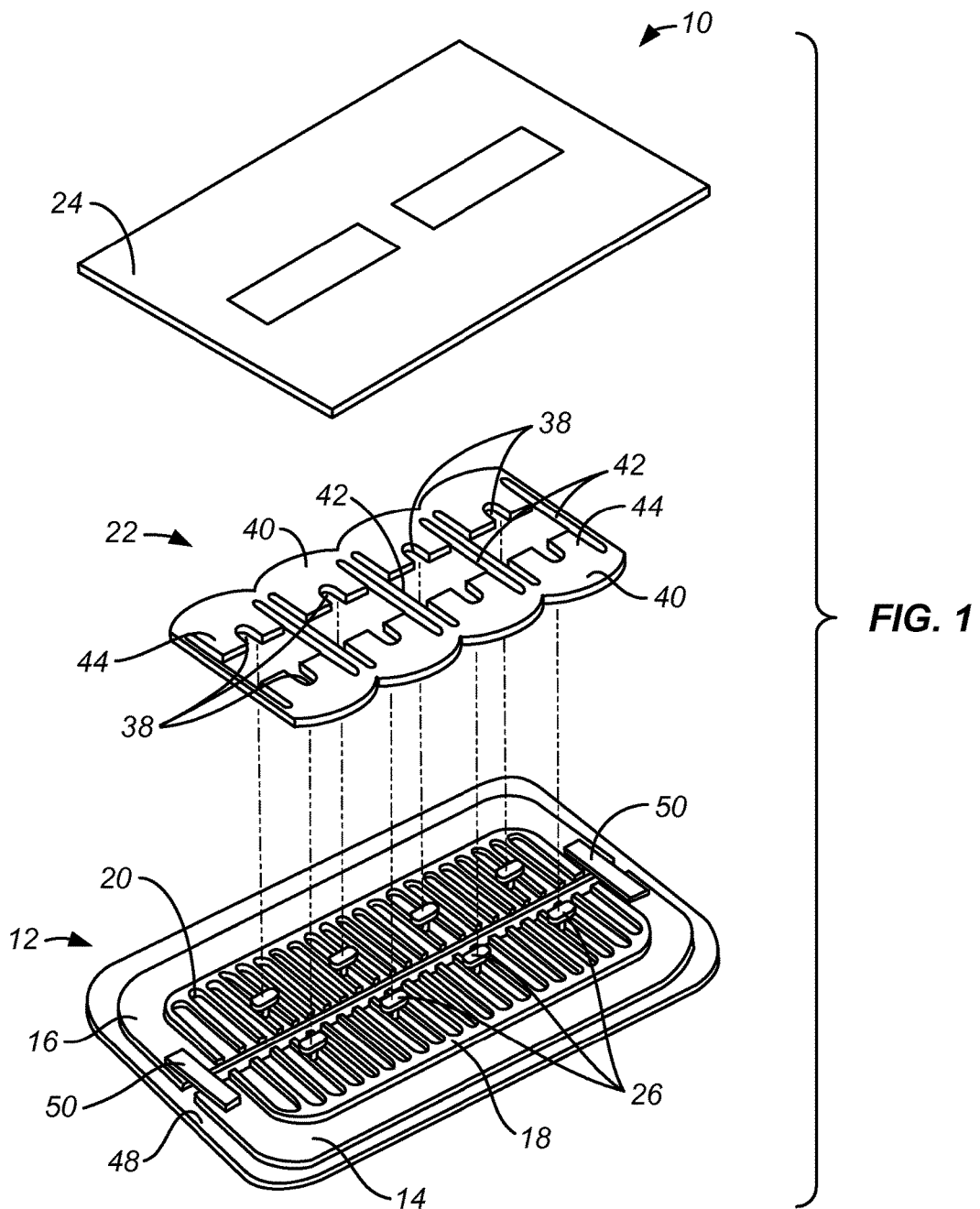
FIG. 1 is an exploded view of an incision closure appliance constructed in accordance with the principles of the present invention.
Figure 2:
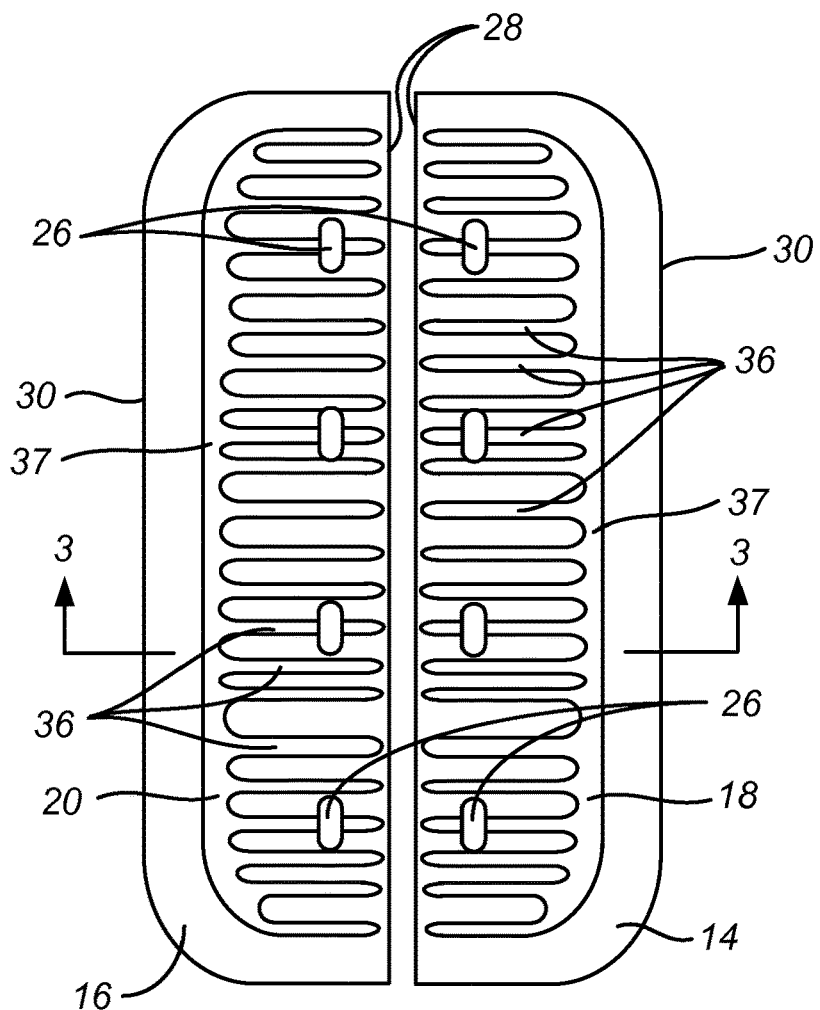
FIG. 2 is a top view of the assembly of a base and a force distribution structure which is part of the incision closure appliance.
Figure 3:
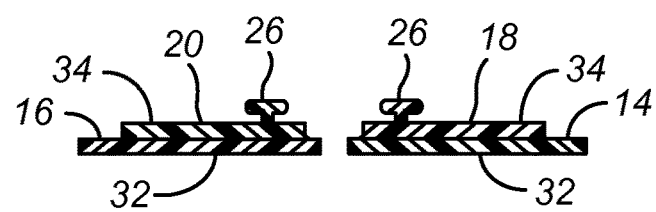
FIG. 3 is a cross-sectional view taken along line 3-3 of FIG. 2.

Referring now to FIGS. 1-3, an incision closure appliance 10 comprises a base assembly 12 including a right panel 14 and a left panel 16. A right force distribution structure 18 is secured to the right panel 14, typically by laminating the force distribution structure to an upper surface of the panel, and a left force distribution structure 20 is similarly attached to an upper surface of the left panel 16. The incision closure appliance further comprises a closure component 22 which is removably attachable to the right and left forced distribution structures 18 and 20 in order to close an incision, as described in more detail below, and the appliance is completed with an optional securing layer 24 which may be placed over the combined base assembly 12 and closure component 22 after they have been secured to the patient and the incision has been closed by drawing the panels together using the closure component.

The closure component 22 is intended and adapted to draw the inner portions of the force distribution structures 18 and 20 inwardly toward each other to close a surgical incision which has been formed therebetween. In the illustrated embodiment, a plurality of cleats 26 are formed on lateral supports 36 which are held axially by spine 37 of the force distribution structures 18 and 20. The cleats 26 are received in slots 38 formed along inner edges of opposed engagement members 40 of the closure component 22. The opposed engagement members 40 are held together by lateral struts 42 so that the engagement members are held at a fixed, laterally spaced-apart distance (in other embodiments the spaced-apart distance may be adjustable). The slots 38 are preferably formed on flexible tab-like structures 44 which allow the slots to be pulled upwardly over the corresponding cleats in order to secure the closure component 22 over the force distribution structures 18 and 20.

The lower surfaces 32 of each panel 18 and 20 will typically be covered with a pressure-responsive adhesive, where the adhesive is initially covered with a protective layer 48 which may be peeled away immediately prior to use. Additionally, pull-away tabs 50 or other similar structures may be provided in order to hold the right and left panels 14 and 16 together at a pre-determined spaced-apart distance after the layer 48 has been removed but prior to adhering the panels to a patient's skin or other tissue surface. It is important that the distance between the inner edges 28 of each panel 14 and 16 be maintained as close as possible to the original target spacing so that the tissue edges, when closed by the closure component 22, will be precisely brought together, typically with a slight eversion.

Figure 4:
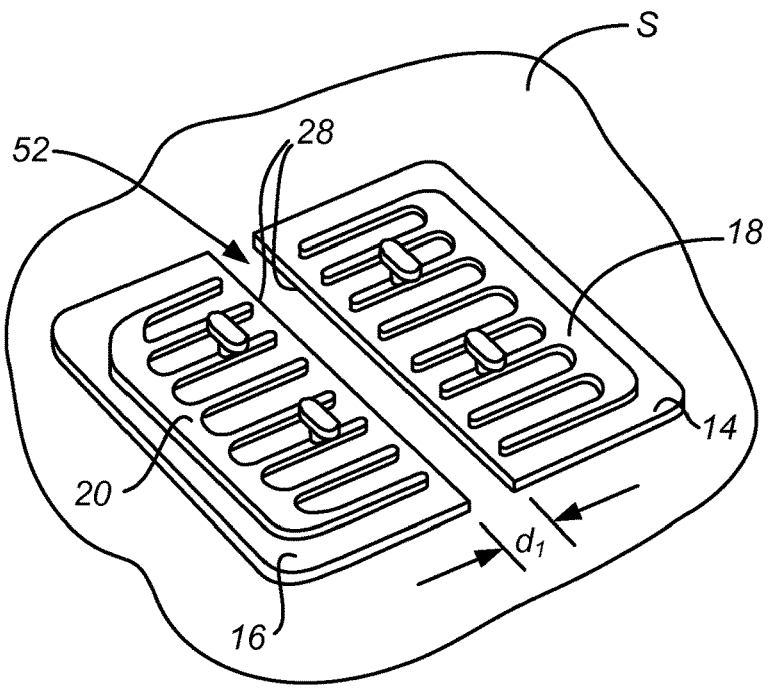
FIGS. 4-7 illustrate use of the incision closure appliance of the present invention for forming and closing an incision in a patient's skin.

Referring now to FIGS. 4 through 7, a protocol for both forming an incision and subsequently closing the incision in accordance with the principles of the present invention will be described. Initially, the right and left panels 14 and 16 are placed on the patient's skin followed by reference letter S, as shown in FIG. 4. The panels 14 and 16 are applied by first pulling away the protective layer 18 and placing the panels onto the tissue, after which time the tabs 50 may be removed, leaving an incision path 52 defined between the inner edges 28. The spacing of the inner edges 28 will be selected to provide a fixed, pre-determined distance $d_1$.

Figure 5:
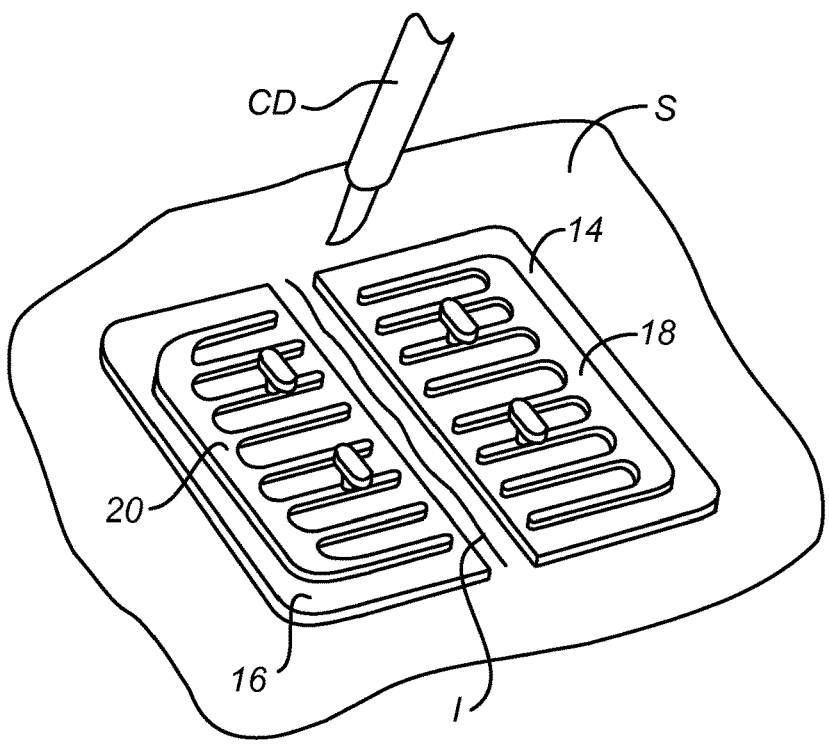

After the right and left panels 14 and 16 are in place, an incision I can be formed in the space between the panels using a scalpel or other surgical cutting device CD, as shown in FIG. 5.

Figure 6:
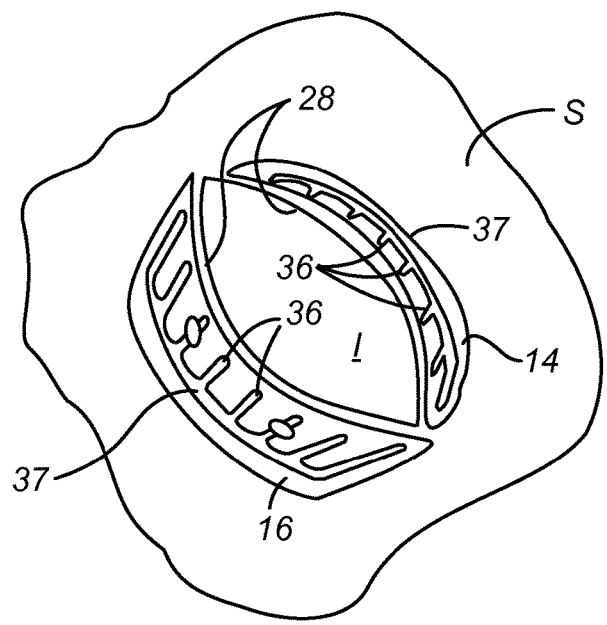

After the incision I is made, a surgical procedure may be performed by opening the inner edges of the incision which in turn deforms the inner edges 28 of the right and left panels 14 and 16, as shown in FIG. 6. As the inner most ends of the supports 36 are not connected, they are free to separate and allow the elastic matrix of the right and left panels 14 and 16 to expand, as clearly in FIG. 6. The dimensional stability of the remainder of the panels, however, will be preserved by the lateral supports 36 as well as the axial spines 37 which do not elongate under the influence of the force applied by stretching opening the incision.

Figure 7:
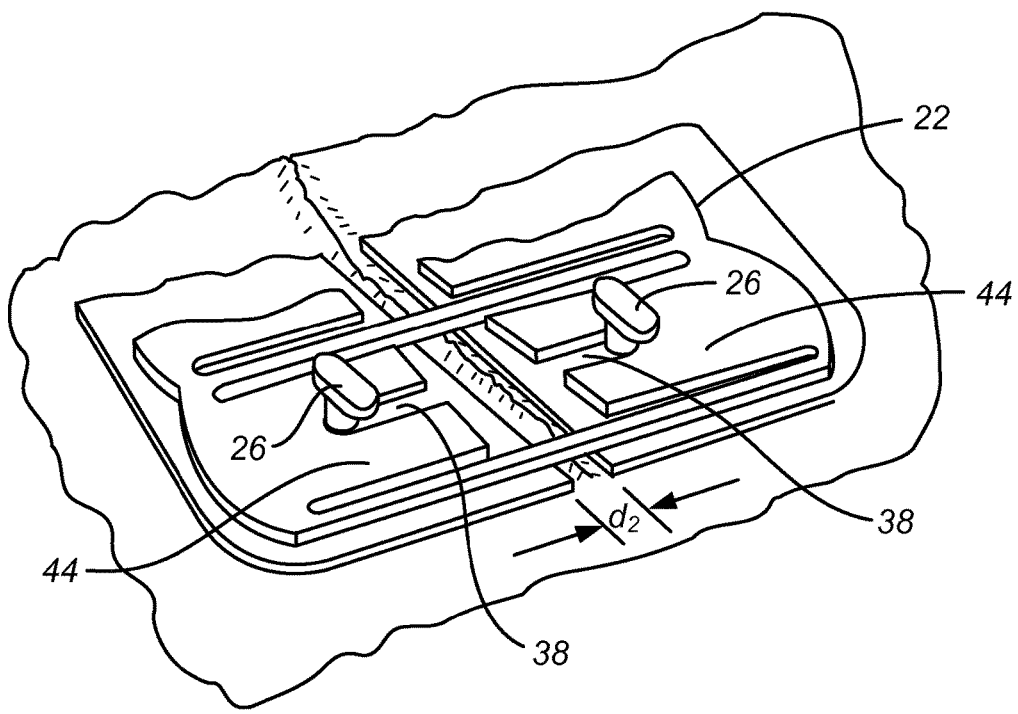

After the surgical procedure is complete, the closure component 22 will be secured over the force distribution structures 18 and 20, as illustrated in FIG. 7. In particular, the slots 38 in the tab-like structures 44 are engaged over opposed cleats 26 in order to draw opposed edges of the panels as well as of the tissue incision together. By properly spacing the depth of the slots 38, the closure component 22 can be tailored so that the panels 14 and 16 are brought together by a pre-selected distance $d_2$. Typically, the distance $d_2$ will be less than the initial separation $d_1$ so that the inner edges of the tissue are brought together to cause the tissue edges along the incision to slightly evert (pucker upwardly) which can improve healing and reduce scarring.

Figure 8:
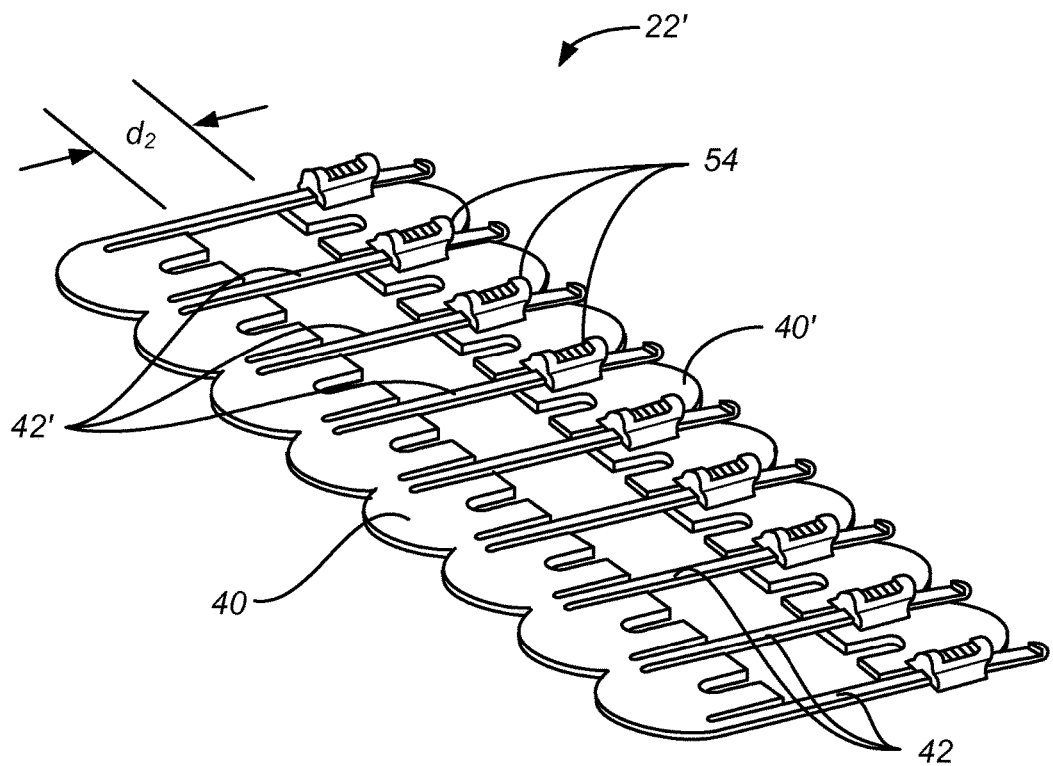
FIG. 8 illustrates an alternative construction of a closure component for the closure appliance of the present invention.

Optionally, as shown in FIG. 8, a closure component 22' may include engagement members 40', where one end of each lateral strut 42' is joined by an adjustable clasp or other mechanism 54 so that the distance between the inner edges of the opposed engagement members 40' can be adjusted in order to increase or lessen the distance $d_2$ therebetween.

Figure 9:
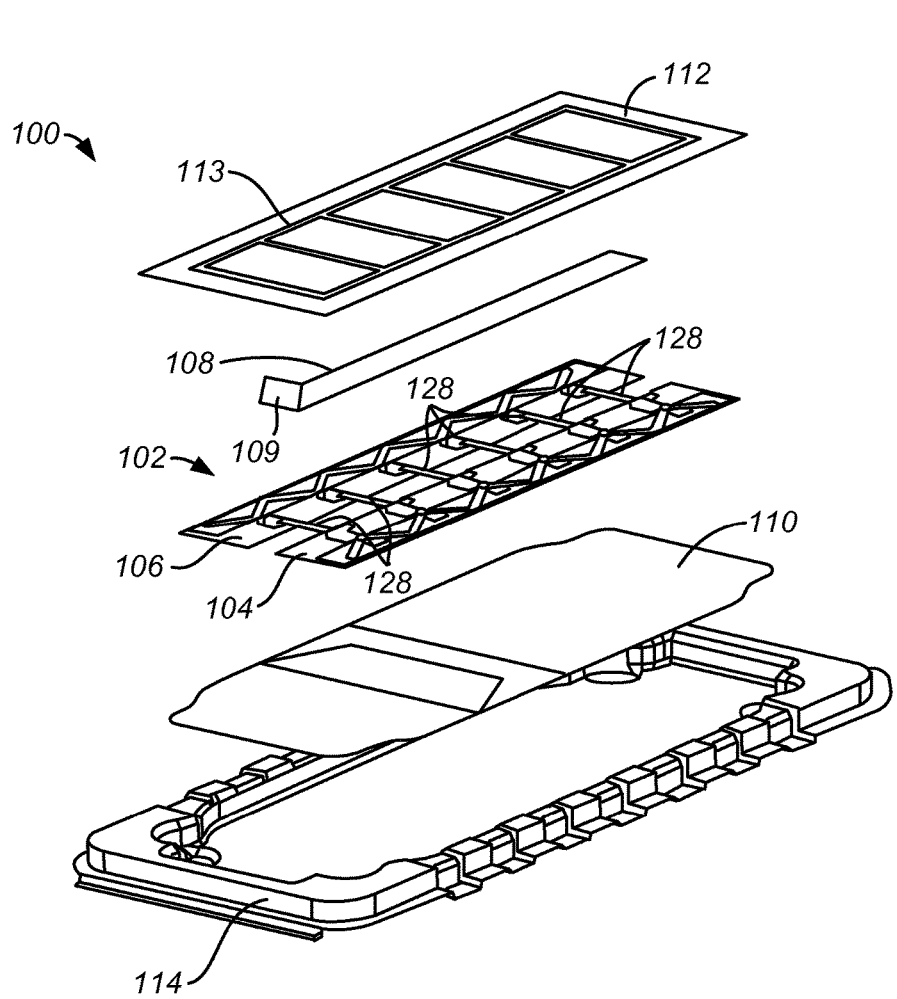
FIG. 9 is an exploded view of a further embodiment of an incision closure appliance constructed in accordance with the principles of the present invention.
Figure 10:
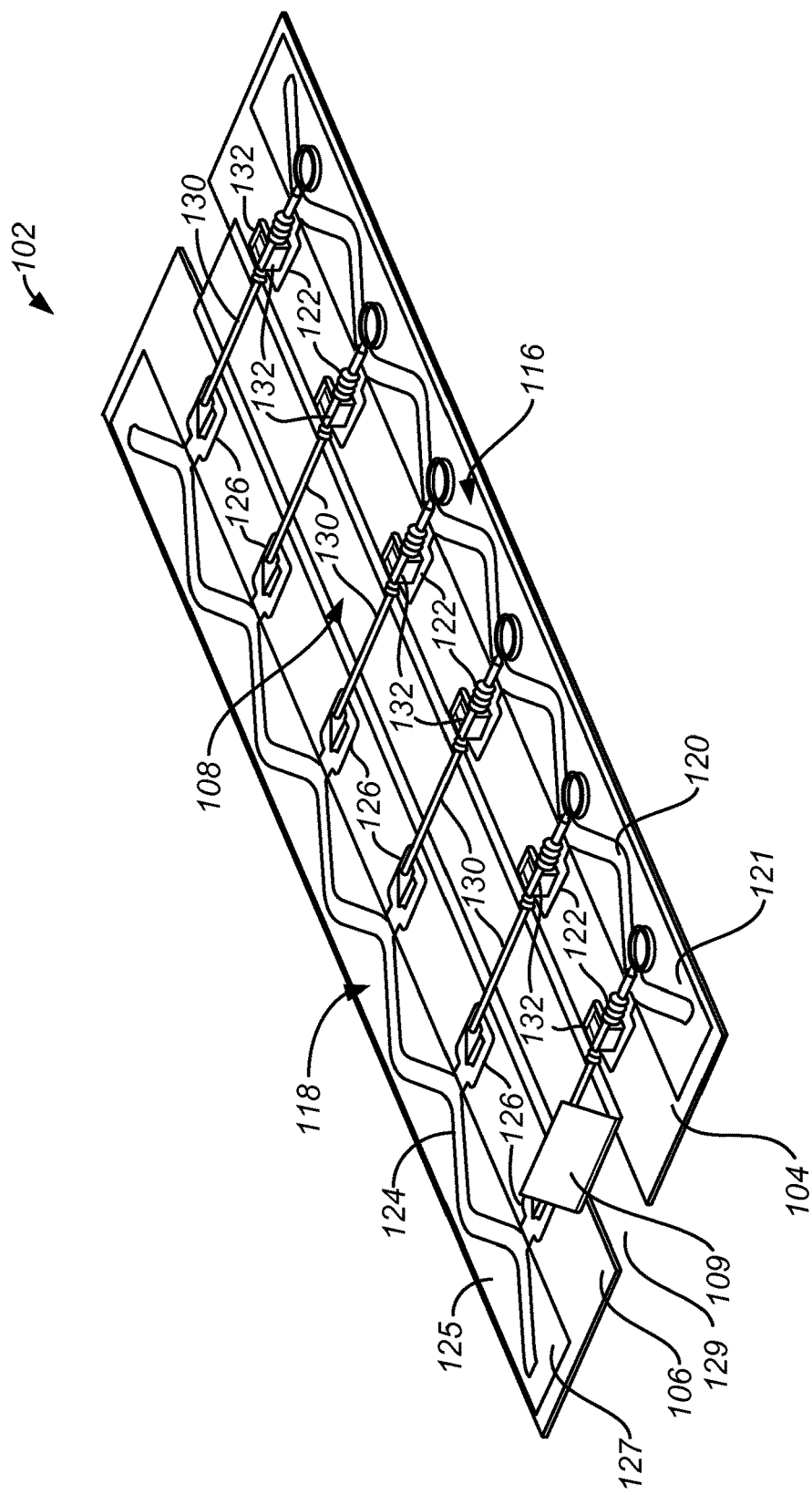
FIG. 10 is an enlarged isometric view of the base and force distribution structure of the system of FIG. 9.

An alternative embodiment 100 of the incision closure appliance of the present invention is illustrated in FIGS. 9 and 10. The appliance 100 includes a base assembly 102 having a right panel 104 and a left panel 106. A positioning or alignment strip 108 is provided to secure the inner edges of each panel together, as shown best in FIG. 10 and includes an end tab 109 that allows the user to pull the strip from the panels 104 and 106 after the panels have been put in place on a tissue surface.

The incision closure appliance 100 further includes a backing 110 having an end which may be partially folded back to expose an underlying adhesive backing on the panels and allow that end of the base assembly 102 to be adhered to the tissue while the remainder of the base assembly is still covered by the backing. A securing layer 112 which includes a reinforcement frame 113 is provided for placement over the right panel 104 and left panel 106 after the base assembly 102 has been closed over an incision, generally is described in connection with the previous embodiment. Usually, a holding tray 114 will be provided for maintain the components of the appliance together in a sterilized condition where the tray 114 will be covered with conventional medical packaging cover.

As illustrated in FIGS. 9 and 10, a right force distribution structure 116 and a left force distribution structure 118 are provided on the upper surfaces of the right panel 104 and the left panel 106, respectively. The right force distribution structure 116 includes a right axial spine 120 and a plurality of lateral supports 122. Typically, the right axial spine 120 comprises a serpentine or zig-zag number which is embedded in or laminated to a base strip 121. The serpentine axial spine 120 would typically be formed from a flexible, resilient plastic, typically a hard plastic, while the base strip 121 will be comprised of a polyurethane or similar plastic layer. The lower surface of the polyurethane layer will be covered with a hydrocolloid layer for tissue adhesion. The structure of the left forced distribution structure 118 will be the same including a left axial spine 124, left lateral supports 126, and a left base strip 127.

The incision closure appliance 100 will include a closure mechanism comprising a plurality of lateral tie assemblies 128 as shown on FIG. 9. As best seen in FIG. 10, each lateral tie assembly 128 will include a rod which is secured at one end to the left lateral support 126 and a ratchet mechanism 132 which is secured to the right lateral support 122. Each rod 130 will usually be aligned with the axis of the left panel 106 parties so that a gap 129 between the right panel 104 and left panel 106 will be left open so that an incision can be made there between. After the incision is made, each rod 130 will be pulled over to the associated ratchet 132 on the right panel 104. A series of ratchet rings on each rod will be pulled into the associated ratchet mechanism 132, and the rod then pulled laterally until the desired closing tension is applied at that point along the base assembly 102. It is a particular advantage that each of the lateral tie assemblies 128 may be individually adjusted to supply the desired closing tension across the tissue along the length of the incision being closed. Once the desired closing tension has been provided along the entire incision, the securing layer 112 may be placed over base assembly 102 to hold the appliance and tissue in place.

Referring now to FIGS. 11A and 11B, an alternative design for the lateral tie assemblies 140 of the present invention is illustrated. These lateral tie assemblies 140 may be utilized with either of the incision closure appliances 10 or 100 described previously. Each lateral tie assembly 140 includes a right force distribution structure 142 and a left force distribution structure 144. The right force distribution structure includes a right spine 146 and a plurality of lateral supports 148. Although three are shown, it will be appreciated that four, five, six or more lateral supports could be included. The left force distribution structure 144 similarly includes a left spine 150 and a plurality of left lateral supports 152. To provide closure, the right force distribution structure 142 includes a rod 154 which extends from the center lateral support 148. Typically, the rod 154 is joined to the support by a live or passive joint 158. A pull loop 156 is provided at the free end of the rod 154, and a plurality of ratchet teeth 162 are provided along the midsection of the rod 154.

The left force distribution structure 144 includes a ratchet mechanism 160 adapted to receive the teeth 162 on the rod 154 of the right force distribution structure. In this way, the rod 154 can be lowered into the ratchet 160 to engage teeth 162, allowing the rod to be pushed forward in order to draw the right and left force distribution structures 142 and 144 together in order to apply tension to the right and left panels.

Figure 12:
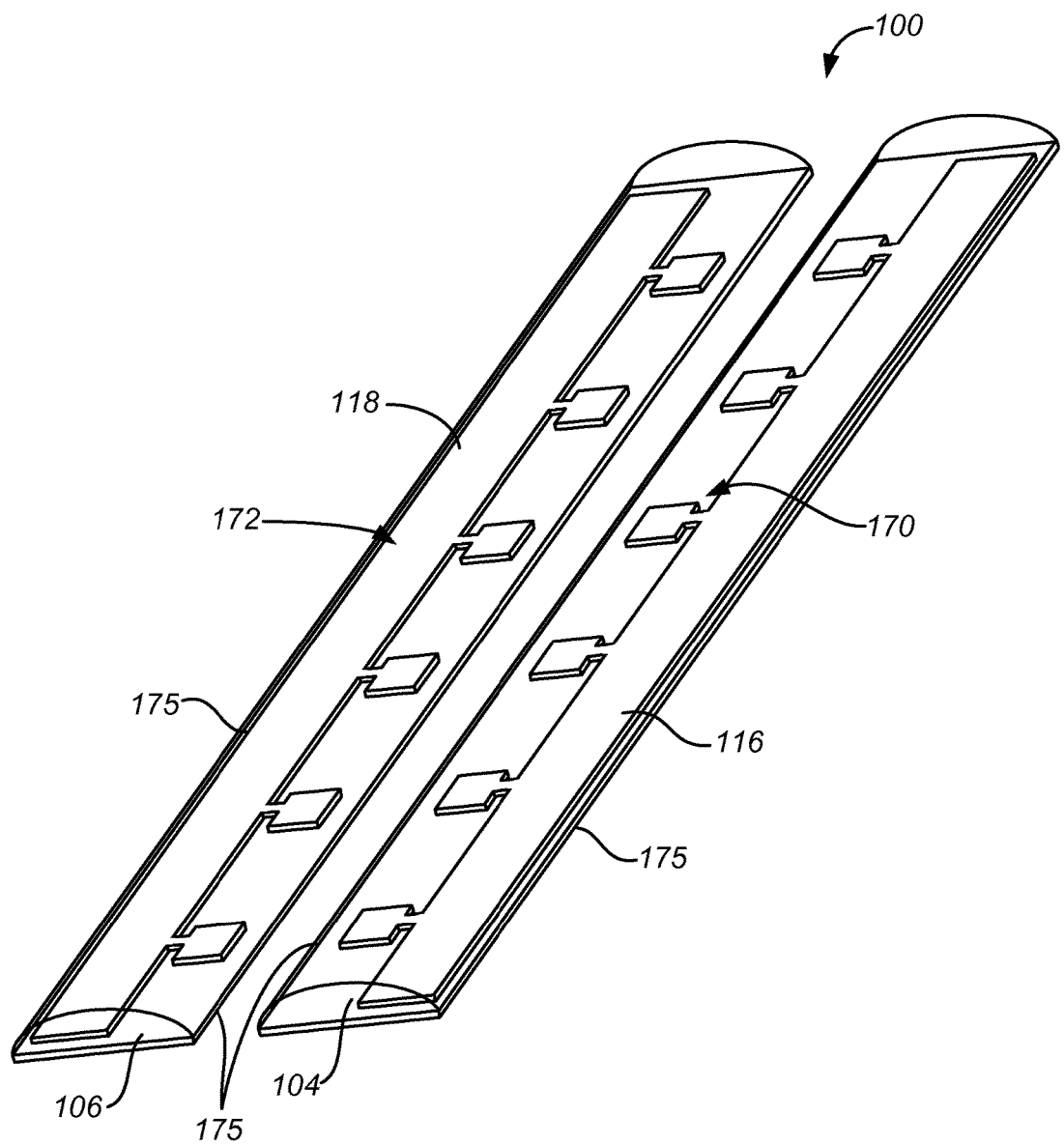
FIG. 12 illustrates a sacrificial cover positioned over an incision closure appliance in accordance with the principles of the present invention.

As illustrated in FIG. 12, a further aspect of the present invention is illustrated. The incision closure appliance 100 is illustrated schematically with only the right and left panels 104 and 106 and the right and left force distribution structures 116 and 118 being illustrated. The remaining system components are not shown for ease of illustration.

The right panel 104 is covered by a right sacrificial cover 170 and the left panel 106 is covered by a left sacrificial cover 172. Each cover 170 and 172 is detachably secured along each edge of the associated base panel so that the covers remain in place during normal handling and placement of the incision closure appliance 100 over the tissue surface to be incised. The use and purpose of these sacrificial covers 170 and 172 is described with reference to FIGS. 13A and 13E.

Figure 13A:
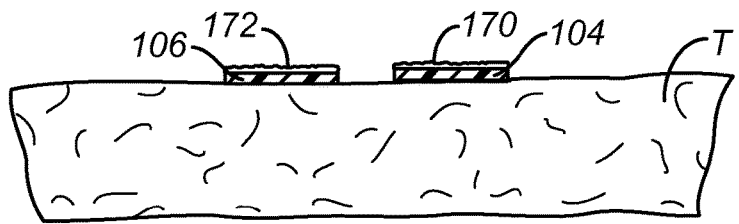
FIGS. 13A through 13E illustrate the principle of operation of the sacrificial cover illustrated in FIG. 12 when used together with a surgical incision drape and performing methods according to the present invention.
Figure 13B:
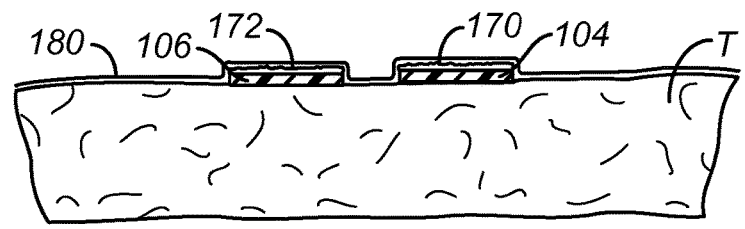
Figure 13C:
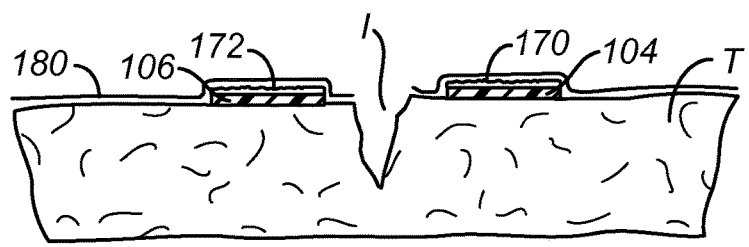

FIG. 13A illustrates the right and left panels 104 and 106 in place on a tissue surface T prior to an incision being made. The right panel 104 is covered by right sacrificial cover 170 and the left panel 106 is covered by left sacrificial cover 172. As is common in many surgeries, an adherent surgical incision drape 180 is placed over the tissue surface T. Any conventional drape may be used such as the Ioban™ antimicrobial incise drape, available from 3M, St. Paul, Minn.

Figure 13D:
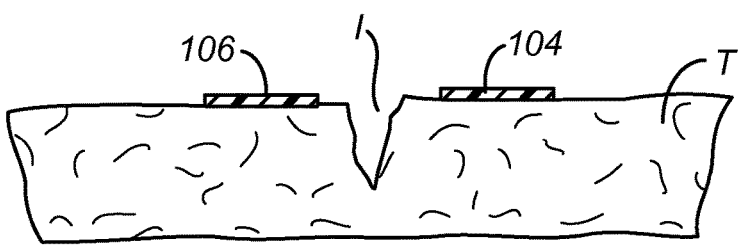
Figure 13E:
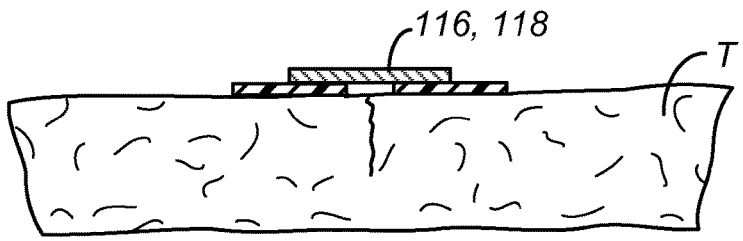

After the incision drape 180 is in place over the incision closure appliance, a surgical incision I may be made for performing a desired surgical intervention. As can be seen, the incision I will cut through the surgical drape 180 between the right and left panels 104 and 106, respectively. After the surgical procedure is completed, the surgical drape 180 will be removed from the tissue surface T. As the surgical drape has a lower adherent surface, prior to the present invention, removal of the drape might have displaced either or both of the right panel 104 and left panel 106. Presence of the sacrificial layers 170m and 172, however, prevents such displacement. Removal of the surgical drape 180 will remove the sacrificial layer 170 and 172, but as each of these layers is configured to break off with a relatively low separation force, removal of the sacrificial layers will not cause the underlying panels 104 or 106 to be displaced. Thus, the panels 104 and 106 will be left in place, as shown in FIG. 13D, and the force distribution structures 116 and 118 can be used as described previously for closing the panels together to close the incision as shown in FIG. 13E.

What is claimed is:

1. An incision closure appliance comprising:
    a base including a left panel and a right panel, each panel having a tissue adherent lower surface, an upper surface, a longitudinal axis, an inner edge, and an outer edge;
    left and right force distribution structures coupled to the left and right panels, respectively, wherein each force distribution structure comprises an axial spine disposed substantially parallel to the longitudinal axis of the left or right panel and a plurality of lateral supports extending laterally from the axial spine and disposed substantially perpendicularly to the longitudinal axis of the left or right panel, wherein the axial spine and the plurality of lateral supports are integral with one another, wherein the lateral supports are axially separate and spaced apart from one another, wherein the force distribution structures are configured to allow the inner edges of the panels to expand while restraining expansion of the outer edges of the panels, and wherein the axial spine and lateral supports are configured to preserve dimensional stability of the panels when the panels are deformed; and
    a closure assembly securable to the left and right panels to draw the inner edges of the panels together, wherein the closure assembly comprises one or more lateral ties, each lateral tie having a fixed end fixedly coupled to one of the left or right force distribution structures and a free end opposite the fixed end, the free end being adjustably coupled to the opposing left or right force distribution structure.

2. An incision closure appliance as in claim 1, wherein each panel of the base comprises an elastic matrix.

3. An incision closure appliance as in claim 2, wherein the elastic matrix comprises an elastomeric membrane, a woven fabric, or a spun fabric.

4. An incision closure appliance as in claim 2, wherein the elastic matrix comprises a fabric woven from elastic elements and having inelastic elements along the outer edge and extending laterally thereacross.

5. An incision closure appliance as in claim 2, wherein the elastic matrix is isotropic.

6. An incision closure appliance as in claim 1, wherein the axial spine of each force distribution structure is disposed axially adjacent to the outer edge of the panel, and wherein the plurality of lateral supports are axially spaced-apart and extend laterally from the axial spine toward the inner edge of the panel.

7. An incision closure appliance as in claim 1, wherein the axial spine and lateral supports are formed from flexible, non-distensible materials.

8. An incision closure appliance as in claim 1, further comprising a removable space maintainer which holds the right and left panels at a fixed distance while they are being adhered to tissue.

9. An incision closure appliance as in claim 8, wherein the removable space maintainer comprises a strip which is removably placed over an axial gap between the right and left panels.

10. An incision closure appliance as in claim 1, wherein the fixed end of each lateral tie is fixedly coupled to the axial spine of the one of the left or right force distribution structures.

11. An incision closure appliance as in claim 1, wherein the free end of each lateral tie is adjustably coupled to the opposing left or right force distribution structure with an adjustable ratchet tightening mechanism.

12. An incision closure appliance as in claim 1, further comprising a securing layer adapted to be placed over an assembly of the base and the closure assembly after the assembly has been secured over an incision on a patient's skin.

13. An incision closure appliance as in claim 12, wherein the securing layer has an inner self-adhesive surface.

14. An incision closure appliance as in claim 1, wherein the fixed end is integral with the one of the left or right force distribution structures.

* * * * *